United States Patent [19]

Nicksic

[11] 4,238,463

[45] Dec. 9, 1980

[54] METHOD FOR DESULFURIZING GASES WITH IRON OXIDE

[75] Inventor: Stephen W. Nicksic, Brea, Calif.

[73] Assignee: Chevron Research Company, San Francisco, Calif.

[21] Appl. No.: 53,123

[22] Filed: Jun. 28, 1979

[51] Int. Cl.³ .............................................. B01D 53/34
[52] U.S. Cl. ..................... 423/226; 423/228; 423/231; 423/573 G; 252/191
[58] Field of Search ............... 423/224, 226, 228, 230, 423/231, 573 G, 573 R, 225, 574 R, 576, 574 G; 252/184, 190, 191

[56] References Cited

U.S. PATENT DOCUMENTS

| Re. 4,998 | 7/1872 | Everett | 423/231 |
|---|---|---|---|
| 76,544 | 4/1868 | St. John | 423/231 |
| 1,105,578 | 7/1914 | O'Donnell et al. | 423/244 |
| 1,479,852 | 1/1924 | Engelhardt | 423/224 |
| 1,507,105 | 9/1924 | Carstens et al. | 423/576 |
| 2,733,979 | 2/1956 | Haensel | 423/225 |
| 3,071,433 | 1/1963 | Dunn | 423/229 |
| 3,822,341 | 7/1974 | Smith | 423/573 G |
| 4,100,257 | 7/1978 | Sartori et al. | 423/226 |

OTHER PUBLICATIONS

Goar, "Today's Gas Treating Processes", Howe-Baker Engineers, Inc., Tyler, Texas, pp. 1-24.

*Primary Examiner*—Earl C. Thomas
*Attorney, Agent, or Firm*—D. A. Newell; W. H. Hooper; W. D. Reese

[57] ABSTRACT

Removal of hydrogen sulfide from gases using iron oxide-containing solids is improved by introducing a liquid containing a primary or secondary amine into the iron oxide-containing solids.

9 Claims, No Drawings

METHOD FOR DESULFURIZING GASES WITH IRON OXIDE

BACKGROUND OF THE INVENTION

The present invention relates to an improved method for removing hydrogen sulfide from gases. More specifically, the present invention relates to an improvement in a method for removing hydrogen sulfide from produced natural gas with iron oxide.

Produced fuel gases such as natural gas and petroleum light gas fractions often contain substantial concentrations of hydrogen sulfide. Normally, the hydrogen sulfide must be removed before the produced gas is suitable for sale or distribution through pipelines, in order to meet the product specifications required by commercial gas suppliers. It is also desirable to remove hydrogen sulfide from fuel gases before they are burned to reduce sulfur oxides emissions. In addition to produced fuel gases, other gases, such as petroleum refinery off-gas streams, are often contaminated with hydrogen sulfide. The presence of hydrogen sulfide can be detrimental when such gases are used in hydrocarbon or petrochemical processing. The presence of hydrogen sulfide also complicates the disposal of refinery gases by, for example, flaring, since the sulfur dioxide produced during burning poses an emissions problem.

Various techniques have been suggested for removing hydrogen sulfide from fuel and other gases. The term "acid gases" include carbon dioxide, as well as hydrogen sulfide, since both these compounds can dissolve in water to form corrosive, acidic solutions. In many cases, conventional purification treatment of gas streams, such as fuel gas streams, has as its purpose the removal of the acid gas components, not just hydrogen sulfide. In such cases, removal of substantial amounts of carbon dioxide in addition to removal of hydrogen sulfide is desirable. On the other hand, produced hydrocarbon gases such as natural gas may contain a substantial amount of carbon dioxide, which is not detrimental to the commercial value of the natural gas. Gas purification processes which remove carbon dioxide from a gas, as well as hydrogen sulfide, may therefore be needlessly complicated and expensive for use in purifying natural gas, and can reduce the volume of natural gas available for sale or distribution. Accordingly, it is sometimes advantageous to remove hydrogen sulfide from natural gas and other produced fuel gases without substantially changing the concentration of carbon dioxide in the gas.

Among the methods proposed for the removal of hydrogen sulfide from gases has been the use of solid, dry materials such as zeolites or iron sponge. The use and regeneration of zeolites is often impractical for processing large quantities of relatively inexpensive natural gas, and zeolites usually remove carbon dioxide as well as hydrogen sulfide. Another technique used for removing hydrogen sulfide from gases has been scrubbing the gases with an aqueous or other liquid solution. Generally, the liquid materials such as aqueous solutions of amines, alkanolamines, potassium carbonate and the like, which have been used to remove hydrogen sulfide from gases by liquid phase scrubbing also remove substantial amounts of carbon dioxide. These aqueous and other liquid aqueous scrubbing processes usually operate by forming a chemical addition product from hydrogen sulfide and, for example, an amine in liquid solution and then stripping the hydrogen sulfide out of the liquid solution in concentrated form. Disposal of this concentrated hydrogen sulfide usually requires a Claus unit, or the like, for converting the hydrogen sulfide to sulfur. Some types of liquid scrubbing-type purification processes actually require a substantial concentration of carbon dioxide in the gas to be treated for operability in desulfurization. Various other solvents, which may be termed physical solvents for hydrogen sulfide, have also been employed or suggested. Generally, these physical solvents simultaneously remove carbon dioxide from the gas, in addition to hydrogen sulfide. Direct conversion of hydrogen sulfide to sulfur in aqueous or other liquid solutions has also been proposed. For example, it has been suggested to dissolve hydrogen sulfide in an alkaline solution and to oxidize the hydrogen sulfide in the liquid solution with one of a variety of oxidation catalysts to provide elemental sulfur in the liquid.

Removal of hydrogen sulfide from gases by contacting them with iron oxide has long been known, and is commercially practiced. Iron oxide has been used in the form of pellets, powder, etc., and has been used on essentially inert solid supports such as wood shavings, clays, etc. Iron oxide on wood shavings, known as iron sponge, is used commercially for removing hydrogen sulfide from produced fuel gases such as natural gas. Iron sponge desulfurization has the advantages of simplicity, economy and ability to remove hydrogen sulfide selectively without affecting carbon dioxide in the gas. Iron sponge desulfurization is sometimes called the "dry-box" process. In natural gas purification, the gas is passed through a bed of iron sponge. Hydrogen sulfide reacts with iron oxide (e.g., ferric oxide) to form iron sulfide (e.g., ferric sulfide). Enough air is added to the natural gas to provide molecular oxygen to react with the iron sulfide to regenerate the iron oxide and form elemental sulfur. The bed of iron sponge can be used until it becomes plugged or deactivated with elemental sulfur. The deactivated bed is then removed from the purification vessel and discarded. Alkali metal salt solutions may be added to the iron sponge bed periodically to increase its efficiency.

It is often difficult to remove a spent bed of iron sponge from the purification vessel, since the bed tends to harden into a cohesive mass resistant to convenient removal means such as water spraying. Disposal of the spent sponge is often complicated by a sulfurous odor present in the spent sponge. The improvement of the present invention is directed, in part, to overcoming these and other drawbacks in conventional iron-sponge gas-purification methods.

SUMMARY OF THE INVENTION

In an embodiment, the present invention relates to an improvement in a method for removing hydrogen sulfide from a gas, wherein the gas is contacted with a bed of subdivided solids containing iron oxide, hydrogen sulfide is reacted with iron oxide to form iron sulfide; iron sulfide is reacted with molecular oxygen in the gas to form iron oxide and elemental sulfur; elemental sulfur is deposited in said bed; and the gas is recovered from the bed, the improvement comprising: introducing into the bed a liquid comprising an amine having the formula

where $R^1$ and $R^2$ are selected from hydrocarbon radicals having from 1 to 10 carbon atoms, and where $R^1$ may be hydrogen ion.

I have found that addition of a primary or preferably a secondary amine to a bed of iron sponge used for removing hydrogen sulfide from natural gas has several surprising and beneficial effects. The life of the iron sponge appears to be increased. The spent iron sponge does not form a hard, cohesive mass and can be removed from the purification vessel easily. The pressure drop through the iron sponge bed is reduced. The spent sponge has essentially no detectable sulfurous odor, facilitating disposal of the used material.

DETAILED DESCRIPTION OF THE INVENTION

The improved method of the present invention is directed to the removal of hydrogen sulfide from a gas. Gases conventionally treated with iron oxide to remove hydrogen sulfide can suitably be purified. Gases which can suitably be treated for the removal of hydrogen sulfide include, for example, methane, ethane, propane, isopropane, n-butane, isobutane, and like paraffins, ethene, propylene, and like olefins, carbon dioxide, molecular nitrogen, molecular oxygen, molecular hydrogen and water vapor. The method of the invention is particularly adaptable for removing hydrogen sulfide from natural gas and light gas fractions of petroleum, which typically contain a major proportion of methane, along with a mixture of paraffins and olefins. Produced hydrocarbon fuel gas usually also contains at least a substantial amount of carbon dioxide. For various reasons, air often becomes mixed with produced hydrocarbon gases, such as natural gas, during their gathering and transmission. A mixture of natural gas and air can suitably be treated according to the present invention. Preferably mixtures of gaseous hydrocarbons with carbon dioxide, nitrogen, oxygen, water vapor, hydrogen, and the like are subjected to hydrogen sulfide removal.

According to the invention, a liquid containing a primary or preferably a secondary amine is added to a bed of iron oxide. Amines suitable for use in the present invention have the general formula

where $R^1$ and $R^2$ can each be a hydrocarbon radical selected from $C_1$-$C_{10}$ hydrocarbons, and wherein $R^1$ may be hydrogen ion. Suitable hydrocarbon radicals include methyl, ethyl, propyl, benzyl, cycloalkyl, and the like. Preferred alkyl radicals include 2-propyl, 2-n-butyl, 3-n-pentyl, 3-methyl, 2-butyl and cyclohexyl. Preferably, a carbon atom in at least one of $R^1$ and $R^2$ is bonded to the nitrogen atom of the amine, and to two other carbon atoms, so that the carbon atom is bonded to a single hydrogen atom. Aromatic substituent radicals should be separated from the nitrogen component of the amine by at least one carbon atom. Amines which are suitable for use in the present process are preferably those which have a substantial vapor pressure at the temperature and pressure employed in the operation. Secondary amines are particularly preferred. It will be within the ability of those skilled in the art to select an amine having a substantial vapor pressure in relation to the particular purification conditions used.

If molecular oxygen is not already present in the gas to be purified by hydrogen sulfide removal with the iron oxide, molecular oxygen is conventionally added to the gas prior to the purification treatment. Preferably, the concentration of molecular oxygen in the gas is adjusted to be at least sufficient to permit conversion to elemental sulfur of all the sulfur present in the hydrogen sulfide in the gas according to the stoichiometric reaction of oxygen and hydrogen sulfide to form water and sulfur. In removing hydrogen sulfide from a fuel gas by the improved procedure of the invention, enough air should be mixed with the fuel gas to provide the desired amount of molecular oxygen for reaction with the iron sulfide, e.g., one mol of molecular oxygen for each two mols of hydrogen sulfide present in the gas. It will be apparent to those skilled in the art that the concentration of molecular oxygen required will depend, in part, on the degree of hydrogen sulfide removal which is desired. When complete removal of hydrogen sulfide is desired, it is preferred to include at least the stoichiometric amount of molecular oxygen, and particularly preferably at least 1.5 times the stoichiometric amount of molecular oxygen required for complete conversion of all the hydrogen sulfide. In cases when a relatively large concentration of molecular oxygen is already present in the gas to be treated, with respect to the hydrogen sulfide concentration, e.g., when air or pure oxygen is to be purified, it is obviously not necessary to add molecular oxygen to the gas to be treated. When addition of molecular oxygen is necessary, a molecular oxygen-containing gas such as air can be metered into the gas to be purified by any well-known means at the desired rate.

Conventional purification conditions may be employed in the improved operation, including a temperature in the range from 0° C. to 200° C. Preferably a temperature between 25° C. and 100° C. is employed. Conventional purification conditions also include pressures between atmospheric and 50 atmospheres. Preferred pressures are those between atmospheric and 20 atmospheres. Conventional purification contact times of from 0.001 minute to 10 minutes are suitable for carrying out the purification treatment. Preferably a purification time between 0.01 minute and 5 minutes is employed.

The iron oxide can be used in any convenient solid, subdivided form, e.g., as pellets, extended on solid supports, etc. Preferably, the iron oxide is disposed on a cellulosic support such as wood shavings. The iron oxide is preferably in the form of ferric oxide, but less-oxidized forms of iron can be used, since they can be oxidized to ferric oxide simply by contact with oxygen at moderate temperature. A variety of suitable conventional forms of iron oxide will be apparent to those skilled in the art.

The iron oxide-containing solid is preferably formed into a bed through which a stream of the gas to be purified is passed. Batch-type contact between the gas and solid bed can be used, but is not practical for most purposes. Conventional purification apparatus can suitably be used for holding the bed of solids and effecting contact between the gas and iron oxide-containing solids.

According to the invention, a liquid including an amine, preferably a secondary amine, is introduced into the bed. The amine can be introduced continuously or intermittently in either a single treatment or a plurality of periodic treatments. The amine-containing liquid can be any convenient amine, or solution or suspension of an amine such as a water solution, but is preferably a non-aqueous liquid having the amine in solution. A preferred non-aqueous solvent is dimethylsulfoxide. The concentration of the amine in a solvent liquid is not critical. A pure liquid amine can be used, or a dilute amine solution can be used. In aqueous solutions, a saturated solution of the amine is preferably used. It is preferred to introduce relatively small quantities of the amine into the bed of iron oxide periodically, e.g., weekly or daily.

The amount of amine added to the iron oxide at any given time is preferably from about 0.01 part per million, by weight, to about 1 weight percent of the iron oxide present in the bed being treated. The quantity of amine-containing liquid used should be sufficient, during a given treatment, to wet a substantial portion of the bed, and preferably enough liquid is used in each treatment so that more than one-half of the bed is wetted.

EXAMPLE

The improvement of the invention was employed in a conventional iron sponge unit in commercial natural gas purification service. Prior to introduction of the amine, removal of spent sponge was found to be extremely difficult and time-consuming, and the spent iron sponge had a distinctly unpleasant sufurous odor. The life of a bed of iron sponge was felt to be undesirably short. According to the invention, a saturated aqueous solution of equal volumes of ethylcyclohexylamine and N-isopropylcyclohexyamine was added to the soda ash liquid normally used to maintain an alkaline condition in the bed. The amine solution was added to the iron sponge bed every 7 days. Each treatment included about 40 cc of total amine. The amine treatment was continued for about 90 days. The useful life of the iron sponge bed in use was substantially increased. When the iron sponge became spent, it was found to be easily removable with a low-velocity water spray, and the spent iron sponge had essentially no odor. The pressure drop was reduced from 10–15 psi to 4–5 psi.

A preferred embodiment of the invention having been described in the foregoing example, a variety of modifications, variations and equivalents of the invention will be apparent to those skilled in the art. These modifications and equivalents are intended to be included within the scope of the invention as defined in the appended claims.

What is claimed is:

1. In a method for removing hydrogen sulfide from a gas, wherein said gas is contacted with a bed of subdivided solids containing iron oxide, hydrogen sulfide is reacted with iron oxide to form iron sulfide; iron sulfide is reacted with molecular oxygen in said gas to form iron oxide and elemental sulfur; elemental sulfur is deposited in said bed; and said gas is recovered from said bed, the improvement comprising: introducing into said bed a liquid comprising an amine having the formula

where $R^1$ and $R^2$ are selected from hydrocarbon radicals having from 1 to 10 carbon atoms, and where $R^1$ may be hydrogen ion.

2. An improved method according to claim 1 wherein said bed of solid comprises ferric oxide disposed on a cellulosic support.

3. An improved method according to claim 1 wherein a carbon atom in at least one of $R^1$ and $R^2$ is bonded to (a) the nitrogen atom of said amine, (b) two other carbon atoms, and (c) a hydrogen atom.

4. An improved method according to claim 1 wherein said gas includes at least one compound selected from a $C_1$–$C_4$ paraffin, a $C_1$–$C_4$ olefin, carbon dioxide, molecular nitrogen, molecular oxygen, molecular hydrogen and water vapor.

5. An improved method according to claim 1 wherein at least one of $R^1$ and $R^2$ is selected from 2-propyl, 2-n-butyl, 3-n-pentyl, 3-methyl-2-butyl and cyclohexyl.

6. An improved method according to claim 1 wherein said gas is a produced fuel gas.

7. An improved method according to claim 1 wherein said liquid comprises an aqueous solution of said amine.

8. An improved method according to claim 1 wherein said liquid comprises a solution of said amine in dimethylsulfoxide.

9. An improved method according to claim 1 wherein said amine is a secondary amine.

* * * * *